United States Patent [19]

Ueno et al.

[11] Patent Number: 4,831,158

[45] Date of Patent: May 16, 1989

[54] PREPARATION PROCESS OF INDOLES

[75] Inventors: Tomoyuki Ueno, Yokohama; Tadatoshi Honda, Hiratsuka; Takashi Jimbo, Yokohama; Makoto Kotani, Yokohama; Kazuhiro Terada, Yokohama; Shinji Kiyono, Yokohama, all of Japan

[73] Assignee: Mitsui Toatsu Chemicals, Incorporated, Tokyo, Japan

[21] Appl. No.: 117,904

[22] Filed: Nov. 2, 1987

Related U.S. Application Data

[63] Continuation of Ser. No. 793,143, Oct. 31, 1985, abandoned.

[30] Foreign Application Priority Data

Nov. 8, 1984 [JP] Japan ................................. 59-234083
Nov. 12, 1984 [JP] Japan ................................. 59-236724

[51] Int. Cl.$^4$ ............................................. C07D 209/08
[52] U.S. Cl. ...................................................... 548/508
[58] Field of Search ........................................ 548/508

[56] References Cited

U.S. PATENT DOCUMENTS

| | | | |
|---|---|---|---|
| 4,159,271 | 6/1979 | Sano | 548/508 |
| 4,456,760 | 6/1984 | Matsuda et al. | 548/508 |
| 4,476,310 | 10/1984 | Honda et al. | 548/508 |

FOREIGN PATENT DOCUMENTS

| | | | |
|---|---|---|---|
| 9046267 | 3/1984 | Japan | 548/508 |
| 9055869 | 3/1984 | Japan | 548/508 |
| 9073567 | 4/1984 | Japan | 548/508 |

OTHER PUBLICATIONS

Ube Industries, Derwent and Japio Abstracts of Japanese Patent Application Laid Open No. J58133833, published Aug. 9, 1983.
Patent Abstracts of Japan, vol. 7, No. 248, (Nov. 4, 1983), p. 13C 193, (Oodan).

*Primary Examiner*—Mary E. Ceperley
*Attorney, Agent, or Firm*—Fisher, Christen & Sabol

[57] ABSTRACT

In a process for preparing an indole by reacting an aniline with a diol, a catalyst the activity of which has been reduced through its use in the reaction is brought into contact with an inert gas containing 5 vol. % or less of oxygen so that the catalyst is regenerated for its repeated utilization. The activity of the regenerated catalyst is enhanced further when it is subjected to a reducing treatment for activation upon its reutilization.

11 Claims, No Drawings

PREPARATION PROCESS OF INDOLES

This application is a continuation of application Ser. No. 793,143, filed Oct. 31, 1985, now abandoned.

BACKGROUND OF THE INVENTION

(1) Field of the Invention

This invention relates to a preparation process of indoles from their corresponding anilines and diols, and more specifically to a process for preparing indoles from their corresponding anilines and diols in which catalysts, which have been deteriorated through their use in the reactions, are regenerated for their reutilization.

(2) Prior Art of the Invention

Indoles are known as raw materials for the chemical industry and especially, have become important as raw materials for the synthesis of perfumes and fragrant materials as well as amino acids in recent years.

Numerous attempts have been made to date for the synthesis of indoles. However, they were all accompanied by one or more problems such that lots of by-products were resulted, expensive raw materials were required and/or complex preparation steps were indispensable.

Recently, some catalyst systems effective for reactions, in which indoles are synthesized through fewer steps from economical raw materials, i.e., their corresponding anilines and diols, have been being found. Cu-Cr, Cu-Co, Pd/SiO$_2$, Pt/SiO$_2$, CdS and the like may be mentioned for instance. However, these catalyst systems are all accompanied by one or more drawbacks such that they undergo severe reductions in catalytic activity and/or their catalytic activities are by themselves low. Due to these drawbacks, they are not suited as catalysts for actual application. The present inventors made a variety of investigation on the reactions, and have already reported that the performance of the reactions may be improved by adding water in the reaction systems or effecting the reactions under an elevated pressure.

In addition, the present inventors also revealed that catalyst systems, each of which contains any one of Group Ib metals of the periodic table, i.e., Cu, Ag and Au as an effective component, are effective for the preparation of indoles and allow to conduct the reactions for long time.

Even if these catalysts are employed, they undergo imminent deterioration along the passage of time as the reaction time becomes longer, leading to reductions to their catalytic activities and their selectivities for the intended indoles and hence unavoidably reducing the yields of the indoles.

It is therefore important for the industrial practice of the above-mentioned processes to regenerate their catalysts, which have been deteriorated through their use in the reactions, for their reutilization.

Different regeneration methods may generally be applied depending on the properties of catalysts. No suitable regeneration method has however yet been proposed for catalysts deteriorated in the preparation process of indoles from their corresponding anilines and diols, since the preparation process was developed recently.

As a regeneration method for a catalyst deteriorated through its use in a reaction in which an indole is prepared from its corresponding aniline and diol, it is proposed in Japanese Patent Laid-Open No. 133833/1983 to subject the deteriorated catalyst at a temperature in the range of 300° to 500° C. to a heat treatment in a gaseous (preferably, air) atmosphere containing 5% or more oxygen. As will be demonstrated in Comparative Example 1, Run Nos. 7 and 8, the heat treatment in an atmosphere of air was not able to regenerate the catalytic performance to any sufficient degree and was thus improper as a regeneration method.

SUMMARY OF THE INVENTION

An object of this invention is to provide an industrial process for preparing an indole by reacting its corresponding aniline and diol, in which a catalyst which has been deteriorated through its use in the reaction is regenerated or activated for its reutilization.

When an aniline and a diol are reacted, they are adsorbed on a catalyst employed in the reaction, notably, such as a catalyst containing a Group Ib metal of the periodic table. As the reaction time becomes longer, more and more carbonaceous materials are caused to deposit on the catalyst. As a result, the catalyst is deteriorated. When the thus-deteriorated catalyst is brought into contact at a temperature in the range of 200° to 450° C. with an inert gas containing 5 vol. % or less of oxygen, it is regenerated and rendered ready for reutilization. After the regeneration, the thus-regenerated catalyst may optionally be activated by its reduction so that it can be used repeatedly.

DETAILED DESCRIPTION OF THE INVENTION

Anilines useful in the practice of this invention are represented by the following general formula (I):

wherein R means a hydrogen or halogen atom or a hydroxyl or lower alkyl group. Illustrative of such anilines may include aniline, o-, m- and p-toluidines, o-, m- and p-haloanilines, o-, m- and p-hydroxyanilines, o-, m- and p-anisidines, and so on.

On the other hand, illustrative of such diols may embrace ethylene glycol, propylene glycol, 1,2-butanediol, 1,2,4-butanetriol, glycerol, 2,3-butanediol, diethylene glycol, etc.

The catalyst which is used in the process of this invention contains one or more metals selected from the Group Ib elements, i.e., Cu, Ag and Au as effective components and besides, may optionally contain one or more other elements suitable for incorporation in combination with the above-mentioned effective components, for example, B, C, O, Mg, Al, Si, P, S, Ca, Ti, Cr, Mn, Fe, Co, Ni, Zn, Ga, Ge, Se, Sr, Zr, Mo, Ru, Rh, Pd, Cd, In, Sn, Sb, Te, Ba, La, Ce, W, Ir, Pt, Tl, Pb, Bi, Th and/or the like. These catalyst components may be used as they are or by carrying them on a usual carrier such as diatomaceous earth, activated clay, zeolite, silica, alumina, silica-alumina, titania, chromia, thoria, magnesia, calcium oxide, zinc oxide or the like.

Where Cu and Ag are used as effective components, they may be employed as their nitrates, sulfates, phosphates, carbonates, halides, organic acid salts or the like.

Where Au is used as an effective component, it may be employed as its chloroauric acid, alkali metal chloroaurate, gold cyanide, alkali metal cyanoaurate or the like.

As a preparation method of the catalyst, it is possible to follow the usual kneading method, co-precipitation method or impregnation method. Alternatively, two or more of these methods may be employed in combination. The catalyst may be prepared, for example, by mixing a variety of raw materials, adding a small amount of water and then kneading the resultant mixture in a kneader or the like; by forming various raw materials into an aqueous solution and then adding a precipitant to the aqueous solution to co-precipitate them as an insoluble precipitate; or by impregnating one of various carriers with various raw materials. The thus-obtained catalyst composition is dried, usually, at temperatures below 180° C., added with a suitable granulating additive or forming additive, and then formed. Alternatively, it may be ground as is.

The above-obtained catalyst undergoes gradual deterioration as the reaction time goes on. In the process of this invention, the thus-deteriorated catalyst is thus regenerated by a below-described method, which may optionally be followed by a reducing and activating treatment, for its reutilization.

In the process of this invention, the reaction of an aniline and a diol is effected in the presence of the catalyst in a vapor phase. The reaction may be conducted by any one of the fixed-bed reaction method, fluidized-bed reaction method and moving-bed reaction method. As to the proportions of the aniline and diol which are both introduced into a reactor, it is preferable to feed the diol in an amount of 0.01–5 moles or preferably 0.05–1 mole per mole of the aniline.

The feed rates of the raw materials, i.e., the aniline and diol may be within the range of 0.01–10 $hr^{-1}$ in terms of liquid hourly space velocity (LHSV). It is preferable to introduce them into the reactor after vaporizing them in evaporators beforehand. Upon their introduction into the reactor, steam, hydrogen, carbon monoxide, carbon dioxide, methane, nitrogen, neon, argon or the like may accompany as a carrier gas. Of these carrier gases, steam, hydrogen and carbon monoxide are preferred because they are effective in prolonging the service life of the catalyst.

The reaction temperature may range from 200° to 600° C. with 250° to 500° C. being preferred.

The reaction may be practiced at any pressure, including reduced pressures, normal pressure or elevated pressures. It is however preferred to conduct the reaction at normal pressure or an elevated pressure.

The catalyst, which has been used at least once in the preparation of the indole under the above-described conditions, is regenerated in the following manner for its reutilization. It is preferable to subject the thus-regenerated catalyst to a reducing treatment for activation prior to its reutilization. The regeneration method comprises subjecting the deteriorated catalyst to a heat treatment at 200° to 450° C. in an inert gas containing 5 vol. % or less oxygen.

It is convenient to conduct the regeneration of the deteriorated catalyst without taking it out of the reactor. However, its regeneration may also be effected by taking it out of the reactor.

This heat treatment is intended to remove carbonaceous materials which have been caused to deposit during the reaction and are responsible, at least partly, for the deterioration of the catalyst. The removal of such carbonaceous materials is usually carried out by their combustion reactions, whereby heat is generated. Accordingly, it is desirable to control the temperature of the feed gas (inlet temperature) within 200° to 450° C. or typically within 250° to 400° C. If the temperature is too high, the temperature of the catalyst will become unduly high during its heat treatment due to the above-mentioned exothermic combustion reactions and the effective components in the catalyst will thus undergo sintering, leading to a reduction to its catalytic activity. If the temperature is too low on the other hand, the combustion reactions will not take place or will be difficult to occur and the catalyst will not be fully regenerated.

The gas usable for the above regeneration is an inert gas which contains oxygen in an amount of 5% or less, or preferably 2% or less by volume. If the concentration of oxygen is too high, the combustion reactions will proceed too fast, resulting in a reduction to its catalytic activity. Although no particular lower limitation is imposed on the concentration of oxygen, use of an unduly low $O_2$ concentration will require longer regeneration time. This is certainly disadvantageous from the economical viewpoint. Nitrogen, argon, helium, carbon monoxide, steam or the like may be used as the inert gas. For economical reasons, it is preferred to employ, for the regeneration, a nitrogen-air mixture which contains oxygen at the prescribed level. The flow velocity of the regeneration gas is determined in view of the pressure loss in the catalyst layer and the time required for regeneration. However, it may generally be 5 m/sec. or less, typically, within the range of from 1 cm/sec. to 1 m/sec. As the feeding method of the regeneration gas, an $O_2$-containing inert gas may be fed in the once-through feeding method or a predetermined amount of oxygen may be fed while recirculating an inert gas through the system. No particular limitation is vested on the feeding method of the regeneration gas.

Although the carbonaceous materials deposited on the catalyst can be removed by conducting the above-described regeneration, the regeneration procedure is preferably followed by a further heat treatment in order to ensure the effects of the regeneration. This heat treatment may be effected in the atmosphere of an oxygen-containing gas, preferably, air; at 450° to 600° C., preferably 480° to 550° C. for 5 hours or longer, preferably for about 10–20 hours. By applying this heat treatment, the stability of the catalyst is increased and the reaction can thus be carried out for a long period of time without fluctuation during that time period.

Upon reutilization of the thus-regenerated catalyst, it is more preferable to subject it to a reducing treatment for activation, for example, in the following manner before initiation of the reaction.

In this reducing treatment, hydrogen, carbon monoxide, methanol, ammonia, hydrazine or the like may be used as a reducing agent. Since hydrogen-containing gas is often used as a carrier gas upon preparation of indoles, it is convenient to use hydrogen as a reducing agent.

The reducing temperature may be 100° to 500° C., preferably 200° to 450° C., or more preferably 300° to 400° C. The treatment may be effected at any pressure, including elevated pressures, reduced pressures and normal pressure.

The reducing treatment may be effected for any long time periods. However, the catalytic performance will be leveled off after 2 hours. At an elevated or normal pressure, the reducing treatment may generally be applied for at least 1 minute, or preferably for 30 minutes or longer.

The above-described reducing agents may be used either neat or after being diluted with an inert gas.

By subjecting a catalyst, which has been deteriorated due to its use in the reaction of an aniline and a diol, to heat treatment at 200° to 450° C. in an inert gas containing 5 vol. % or less of oxygen in accordance with the present invention, the carbonaceous deposit can be effectively removed and the activity of the catalyst can thus be restored.

By applying the reducing treatment for activation after the regeneration of the deteriorated catalyst but before reutilization of the regenerated catalyst, the activity of the regenerated catalyst is improved further. The activity achieved by the activation of the regenerated catalyst through its reduction is extremely stable, thereby making it possible to conduct the reaction continuously over a long period of time.

As has been described above, the present invention provides an industrial process for the preparation of an indole from its corresponding aniline and diol in which a catalyst, which has been deteriorated through its use in the reaction of the aniline and diol, is regenerated and optionally activated for its reutilization.

The process of the present invention will hereinafter be described by the following Examples and Comparative Examples.

EXAMPLE 1 and COMPARATIVE EXAMPLE 1

In a tubular reactor made of stainless steel and having an inner diameter of 20 mm, was packed 400 cc of a pellet-like catalyst which had been obtained by causing commercial $SiO_2$ tablets of 3 mm in diameter and 2.5 mm in thickness to carry 13% of silver. While maintaining the tubular reactor at 350° C., a feed gas of aniline, ethylene glycol and water in a molar ratio of 12:1:30 which had in advance been vaporized was fed at 300 g/hr. to the tubular reactor and at the same time, hydrogen gas was also fed at 60 l STP/hr. to the tubular reactor, whereby an indole synthesis reaction was conducted at normal pressure.

After proceeding with the reaction for 25 hours, the catalyst was divided into nine equal portions. They were respectively employed for regeneration tests of the catalyst. Conditions for the regeneration tests are shown in Table 1. Incidentally, the superficial velocity of the oxygen-containing gas in the tubular reactor was 15 Ncm/sec.

Subsequent to the regeneration, each catalyst sample was subjected to a heat treatment for 15 hours in an atmosphere of air. The reaction was resumed under the same conditions as those employed before the regeneration except that the flow velocity of the feed gas and that of hydrogen gas were reduced to one tenth.

With respect to each of the regeneration tests, the conversions of ethylene glycol in the reaction respectively before and after the regeneration and the yield of the resultant indole are shown in Table 1. Incidentally, the conversions of ethylene glycol and the yields of the indole were respectively calculated in accordance with the following equations.

$$\text{Conversion of ethylene glycol} = \frac{\text{The number of moles of consumed ethylene glycol}}{\text{The number of moles of fed ethylene glycol}} \times 100$$

$$\text{Yield of indole} = \frac{\text{The number of moles of the resultant indole}}{\text{The number of moles of fed ethylene glycol}} \times 100$$

In Table 1, the conversions and yields indicate values achieved at the 25th hours of their corresponding reactions (however, the values in parentheses correspond to those achieved at the 50th hours).

TABLE 1

| | Conditions for regeneration | | | |
|---|---|---|---|---|
| | Inlet temperature (°C.) | $O_2$ concentration (Vol. %) | Conversion of ethylene glycol (%) | Yield of indole (%) |
| Example 1 | | | | |
| Before regeneration | — | — | 100 (86.0) | 18.2 (50.7) |
| 1 | 250 | 1.5 | 99.9 | 69.0 |
| 2 | 300 | 1.0 | 100 | 69.1 |
| 3 | 300 | 1.5 | 100 | 68.8 |
| 4 | 300 | 3.0 | 99.8 | 69.5 |
| 5 | 350 | 1.5 | 100 | 68.0 |
| Comp. Ex. 1 | | | | |
| 6 | 190 | 1.5 | 82.0 | 48.1 |
| 7 | 300 | 20.9 | 91.0 | 48.3 |
| 8 | 450 | 20.9 | 84.9 | 39.0 |
| 9 | 500 | 1.5 | 83.0 | 38.8 |

EXAMPLE 2 and COMPARATIVE EXAMPLE 2

Reactions were carried out by following the procedures of Example 1 and Comparative Example 1, inclusive of the regeneration conditions, except that the catalyst was only changed. As a catalyst, was used that obtained by having the same carrier as that of the catalyst used in Example 1 carrying 2.5% of copper.

With respect to each of the regeneration tests, the conversions of ethylene glycol in the reaction respectively before and after the regeneration and the yield of the resultant indole are shown in Table 2.

TABLE 2

| | Conditions for regeneration | | | |
|---|---|---|---|---|
| | Inlet temperature (°C.) | $O_2$ concentration (Vol. %) | Conversion of ethylene glycol (%) | Yield of indole (%) |
| Example 2 | | | | |
| Before regeneration | — | — | 100 (75.0) | 63.5 (41.3) |
| 1 | 250 | 1.5 | 100 | 63.7 |
| 2 | 300 | 1.0 | 99.8 | 64.1 |
| 3 | 300 | 1.5 | 99.7 | 64.5 |
| 4 | 300 | 3.0 | 100 | 64.0 |
| 5 | 350 | 1.5 | 100 | 63.8 |
| Comp. Ex. 2 | | | | |
| 6 | 190 | 1.5 | 72.2 | 39.7 |
| 7 | 300 | 20.9 | 93.0 | 40.9 |
| 8 | 450 | 20.9 | 85.5 | 37.0 |
| 9 | 500 | 1.5 | 87.0 | 37.6 |

EXAMPLE 3

In a tubular reactor made of stainless steel and having an inner diameter of 20 mm, was packed 400 cc of the same catalyst as that employed in Example 1. While maintaining the tubular reactor at 350° C., a feed gas of aniline, ethylene glycol and water in a molar ratio of 12:1:30 which had in advance been vaporized was fed at 300 g/hr. to the tubular reactor and at the same time, hydrogen gas was also fed at 60 l STP/hr. to the tubular reactor, whereby an indole synthesis reaction was conducted at normal pressure. After proceeding with the reaction for 25 hours, the catalyst was regenerated under the following conditions: the inlet temperature of the oxygen-containing gas: 300° C.; the oxygen concentration: 1.5 vol. %; and the superficial velocity in the tubular reactor: 15 Ncm/sec. The thus-regenerated catalyst was then subjected to a heat treatment at 500° C. for 15 hours in an atmosphere of air. Thereafter, the atmosphere was changed to an $N_2$ atmosphere and the temperature was lowered to 320° C. Under these conditions, $H_2$ was fed at 2 l/min. for 1 hour to subject the catalyst to a reducing treatment. The reaction was then resumed under the same conditions as those employed before the regeneration. Upon an elapsed time of 25 hours the conversion of ethylene glycol was 100% while the yield of the resultant indole was 74.2%.

EXAMPLE 4

An experiment was conducted in the same manner as in Example 3 except that the same catalyst as that employed in Example 2 was used.

Upon an elapsed time of 25 hours in the reaction after the regeneration, the conversion of ethylene glycol was 100% while the yield of the resultant indole was 68.9%.

What is claimed is:

1. Process for the preparation of an indole comprising reacting an aniline selected from the group consisting of aniline, o-toluidine, m-toluidine, p-toluidine, o-haloaniline, m-haloaniline, p-haloaniline, o-anisidine, m-anisidine and p-anisidine, with a diol selected from the group consisting of ethylene glycol, 1,2-propylene glycol and 1,2-butanediol, in contact with a catalyst containing at least one of the Group IB metals of the periodic table, the metals being supported on a carrier selected from the group consisting of diatomaceous earth, activated clay, zeolite, silica, alumina, silica-alumina, titania, chromia, thoria, magnesia, calcium oxide and zinc oxide, the catalyst, which has been deactivated through use in the reaction, being brought into contact with an inert gas containing 3 percent or less by volume of oxygen at a temperature of 200° to 450° C. to remove carbonaceous substances deposited on the catalyst, and the catalyst thus regenerated being further heated in an oxygen-containing gas at a temperature of 450° to 600° C. for 5 hours or more subsequent to regeneration, whereby the stability of the catalyst increases to allow the reaction to continue for a long period of time.

2. The process as claimed in claim 1 wherein the oxygen-containing gas is air.

3. The process as claimed in claim 1 wherein the catalyst is Ag supported on a carrrier or Cu supported on a carrier.

4. The process as claimed in claim 1 wherein the inert gas contains 2 percent by volume or less of oxygen.

5. The process as claimed in claim 1 wherein the inert gas is nitrogen.

6. Process for the preparation of an indole comprising reacting an aniline selected from the group consisting of aniline, o-toluidine, m-toluidine, p-toluidine, o-haloaniline, m-haloaniline, p-haloaniline, o-anisidine, m-anisidine and p-anisidine, with a diol selected from the group consisting of ethylene glycol, 1,2-propylene glycol and b 1,2,-butanediol, in contact with a catalyst containing at least one of the Group IB metals of the periodic table, the metals being supported on a carrier selected from the group consisting of diatomaceous earth, activated clay, zeolite, silica, alumina, silica-alumina, titania, chromia, thoria, magnesia, calcium oxide and zinc oxide, the catalyst which has been deactivated through use in the reaction, being brought into contact with an inert gas containing 3 percent or less by volume of oxygen at a temperature of 200° to 450° C. to remove carbonaceous substances deposited on the catalyst, the catalyst thus regenerated being further heated in an oxygen-containing gas at a temperature of 450° to 600° C. for 5 hours or more subsequent to regeneration, whereby the stability of the catalyst increases to allow the reaction to continue for a long period of time, and the thus-heated catalyst being reduced with a member selected from the group consisting of hydrogen, methanol, carbon monoxide, ammonia and hydrazine, at a temperature of 100° to 500° C. to activate the regenerated catalyst.

7. The process as claimed in claim 6 wherein the inert gas contains 2 percent by volume or less of oxygen.

8. The process as claimed in claim 6 wherein the inert gas is nitrogen.

9. The process as claimed in claim 6 wherein the oxygen-containing gas is air.

10. The process as claimed in claim 6 wherein the catalyst is Ag supported on a carrier or Cu supported on a carrier.

11. Process for the preparation of an indole comprising reacting an aniline selected from the group consisting of aniline, o-toluidine, m-toluidine, p-toluidine, o-haloaniline, m-haloaniline, p-haloaniline, o-anisidine, m-anisidine and p-anisidine, with a diol selected from the group consisting of ethylene glycol, 1,2-propylene glycol and 1,2-butanediol, in contact with a catalyst selected from the group consisting of silver supported on a carrier and copper supported on a carrier, the catalyst, which has been deactivated through use in the reaction, being brought into contact with an inert gas containing 3 percent or less by volume of oxygen at a temperature of 200° to 450° C. to remove carbonaceous substances deposited on the catalyst, the thus-regenerated catalyst being heated in air at a temperature of 450° to 600° C. for 5 hours or more subsequent to regeneration, and the thus-heated catalyst is reduced with a member selected from the group consisting of hydrogen, methanol, carbon monoxide, ammonia and monoxide, ammonia and hydrazine, to activate the regenerated catalyst.

* * * * *